US00PP15655P2

(12) United States Plant Patent
Hanes

(10) Patent No.: US PP15,655 P2
(45) Date of Patent: Mar. 15, 2005

(54) ***PETUNIA* PLANT NAMED 'JAM LITBULE'**

(50) Latin Name: *Petunia×hybrida*
Varietal Denomination: Jam Litbule

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 6 days.

(21) Appl. No.: 10/818,376

(22) Filed: Apr. 5, 2004

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—C. A. Whealy

(57) ABSTRACT

A new and distinct cultivar of *Petunia* plant named 'Jam Litbule', characterized by its low trailing, outwardly spreading and mounded plant habit; freely branching habit; freely flowering habit; large single flowers that are violet blue in color; and good garden performance.

1 Drawing Sheet

Botanical classification/cultivar designation: *Petunia×hybrida* cultivar Jam Litbule.

BACKGROUND OF THE INVENTION

The present Invention relates to a new and distinct cultivar of *Petunia* plant, botanically known as *Petunia×hybrida,* and hereinafter referred to by the cultivar name Jam Litbule.

The new *Petunia* is a product of a planned breeding program conducted by the Inventor in Gilroy, Calif. The objective of the breeding program is to create new freely flowering *Petunias* with trailing and spreading plant habit and attractive leaf and flower coloration.

The new *Petunia* originated from a cross-pollination made by the Inventor in September, 2000 of the *Petunia× hybrida* cultivar Celebration Blue Crystal, not patented, as the female, or seed parent, with the *Petunia×hybrida Petunia* cultivar Surfinia Blue, not patented, as the male, or pollen parent. The new *Petunia* was selected as a single plant from the resulting progeny of the cross-pollination in a controlled environment in Gilroy, Calif. in March, 2001.

Asexual reproduction of the new cultivar by terminal vegetative cuttings since March, 2001, in Gilroy, Calif. has shown that the unique features of this new *Petunia* are stable and reproduced true to type in successive generations.

SUMMARY OF THE INVENTION

Plants of the cultivar Jam Litbule have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Jam Litbule'. These characteristics in combination distinguish 'Jam Litbule' as a new and distinct cultivar:

1. Low trailing, outwardly spreading and mounded plant habit.
2. Freely branching habit.
3. Freely flowering habit.
4. Large single flowers that are violet blue in color.
5. Good garden performance.

In side-by-side comparisons conducted in Gilroy, Calif., plants of the new *Petunia* differed from plants of the female parent, the cultivar Celebration Blue Crystal, in the following characteristics:

1. Plants of the new *Petunia* flowered earlier than plants of the cultivar Celebration Blue Crystal.
2. Plants of the new *Petunia* and the cultivar Celebration Blue Crystal differed in flower color as plants of the cultivar Celebration Blue Crystal had violet blue-colored flowers with distinct venation.

In side-by-side comparisons conducted in Gilroy, Calif., plants of the new *Petunia* differed from plants of the male parent, the cultivar Surfinia Blue, in the following characteristics:

1. Plants of the new *Petunia* flowered earlier than plants of the cultivar Surfinia Blue.
2. Flowers of plants of the new *Petunia* were lighter violet blue in color than flowers of plants of the cultivar Surfinia Blue.

Plants of the new *Petunia* can be compared to plants of the cultivar Surfinia Sky Blue, not patented. In side-by-side comparisons conducted in Gilroy, Calif., plants of the new *Petunia* differed from plants of the cultivar Surfinia Sky Blue in the following characteristics:

1. Leaves of plants of the new *Petunia* were narrower than leaves of plants of the cultivar Surfinia Sky Blue.
2. Plants of the new *Petunia* were more freely flowering than plants of the cultivar Surfinia Sky Blue.
3. Flowers of plants of the new *Petunia* were larger and darker in color than flowers of plants of the cultivar Surfinia Sky Blue.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Petunia.*

The photograph at the top of the sheet comprises a side perspective view of a typical plant of 'Jam Litbule' grown in a container.

The photograph at the bottom of the sheet is a close-up view of typical flowers and leaves of 'Jam Litbule'.

DETAILED BOTANICAL DESCRIPTION

Plants of the cultivar Jam Litbule have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the summer with day temperatures ranging from 24 to 29° C., night temperatures ranging from 13 to 18° C. and light levels about 2,000 foot-candles. Plants used for the photographs and description were about 12 weeks from planting rooted cuttings. In the following description, color references are made to The Royal Horticultural Society Colour Chart, 1995 Edition, except where general terms of ordinary dictionary significance are used.

Botanical classification: *Petunia×hybrida* cultivar Jam Litbule.

Parentage:

*Female parent.*—*Petunia×hybrida* cultivar Celebration Blue Crystal, not patented.

*Male parent.*—*Petunia×hybrida* cultivar Surfinia Blue, not patented.

Propagation:

*Type cutting.*—Terminal vegetative cuttings.

*Time to initiate roots, summer and winter.*—About 10 to 12 days at 23° C.

*Time to develop roots, summer and winter.*—About 18 to 23 days at 23° C.

*Root description.*—Fine, fibrous; white in color.

*Rooting habit.*—Freely branching.

Plant description:

*Form.*—Annual flowering plant; indeterminate; initially upright, then low trailing and outwardly spreading; uniformly mounded plant form. Freely branching habit, about eight basal branches each with about three or four lateral branches. Pinching enhances development of lateral branches.

*Usage.*—Appropriate for hanging backets, window boxes, patio containers and landscape applications.

*Plant height.*—About 20 cm.

*Plant diameter* (*area of spread*).—About 56 cm.

*Vigor.*—Vigorous; rapid growth rate.

*Lateral branches.*—Length: About 38 cm. Diameter: About 4 mm. Internode length: About 3 cm. Texture: Pubescent. Color: 144A.

*Foliage description.*—Arrangement: Alternate before flowering; opposite after flowers develop; simple. Length: About 6.7 cm. Width: About 3.4 cm. Shape: Elliptic. Apex: Broadly acute. Base: Attenuate. Margin: Entire. Texture, upper and lower surfaces: Pubescent; glandular. Venation pattern: Pinnate, arcuate. Color: Developing leaves, upper surface: 147B. Developing leaves, lower surface: 147C. Fully expanded leaves, upper surface: 146A. Fully expanded leaves, lower surface: 146B. Venation, upper surface: 147C. Venation, lower surface: 146B. Petiole length: About 6 mm. Petiole diameter: About 4 mm. Petiole color, upper and lower surfaces: 144C.

Flower description:

*Flower type and habit.*—Single salverform flowers; flowers face mostly upward or outward; axillary. Freely flowering habit, about two to three open flowers and about three flower buds per lateral branch at one time.

*Natural flowering season.*—Long day responsive; long flowering period, spring until frost in the autumn; flowering continuous during this period. Plants start flowering about eight weeks after planting rooted cuttings. Flowers persistent.

*Flower longevity on the plant.*—About one week.

*Fragrance.*—Faint, sweet.

*Flower size.*—Diameter: About 6 cm. Tube length: About 3.2 cm. Throat diameter, distal end: About 8 mm. Tube diameter, proximal end: About 4 mm.

*Flower buds.*—Length: About 3.5 cm. Diameter: About 7 mm. Shape: Elongated oblong with ruffled apices. Color: 85A.

*Petals.*—Quantity/arrangement: About five petals fused in a single whorl, funnelform. Length from throat: About 2.7 cm. Width: About 2.4 cm. Shape: Roughly fan-shaped. Apex: Broadly acute. Margin: Entire; undulate. Texture, upper and lower surfaces: Smooth, satiny. Color: When opening, upper surface: 86A. When opening, lower surface: 86C. Fully opened, upper surface: 90B; color becoming closer to 85B with development. Fully opened, lower surface: 85A to 85B. Flower throat (inside): 85A. Flower tube (outside): 144C to 144D. Venation, upper petal surface: 90A. Venation, lower petal surface: 145C. Venation, throat: 79A. Venation, tube: 145C.

*Sepals.*—Arrangement/appearance: Single whorl of five sepals fused at base, star-shaped. Length: About 1.5 cm. Width: About 4 mm. Shape: Ligulate. Apex: Rounded. Margin: Entire. Texture, upper and lower surfaces: Pubescent. Color, upper surface: 146A. Color, lower surface: 146B.

*Peduncles.*—Length: About 2.7 cm. Width: About 1.5 mm. Angle: About 45 to 60° from the stem. Strength: Strong. Texture: Pubescent. Color: 146C.

*Reproductive organs.*—Stamens: Quantity per flower: About five. Anther shape: Ovoid. Anther length: About 2 mm. Anther color: 202C. Pollen amount: Scarce. Pollen color: 194A. Pistils: Quantity per flower: One. Pistil length: About 2.7 cm. Style length: About 2.2 cm. Style color: 144C. Stigma shape: Anvil-shaped. Stigma color: 144A. Ovary color: 145A.

*Seed/fruit.*—Seed and/or fruit production has not been observed.

Disease/pest resistance: Plants of the new *Petunia* have not been noted to be resistant to pathogens or pests common to *Petunia*.

Garden performance: Plants of the new *Petunia* have been observed to have good garden performance. Plants of the new *Petunia* have been noted to tolerate rain, wind and temperatures from 0 to 40° C.

It is claimed:

1. A new and distinct cultivar of *Petunia* plant named 'Jam Litbule', as illustrated and described.

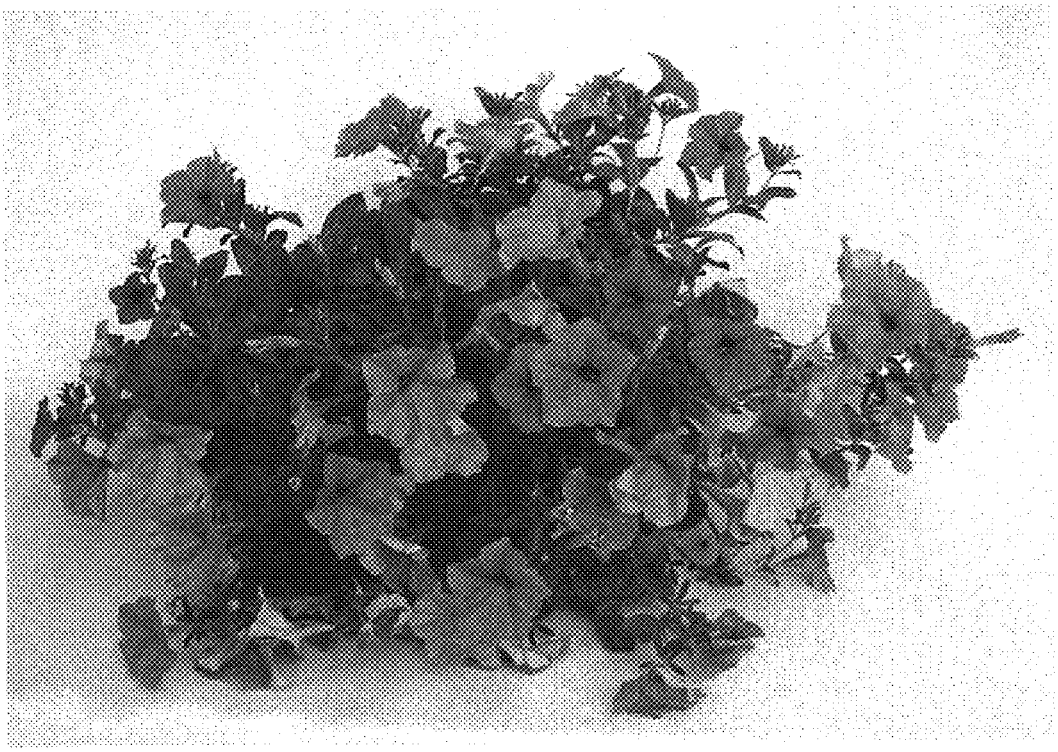
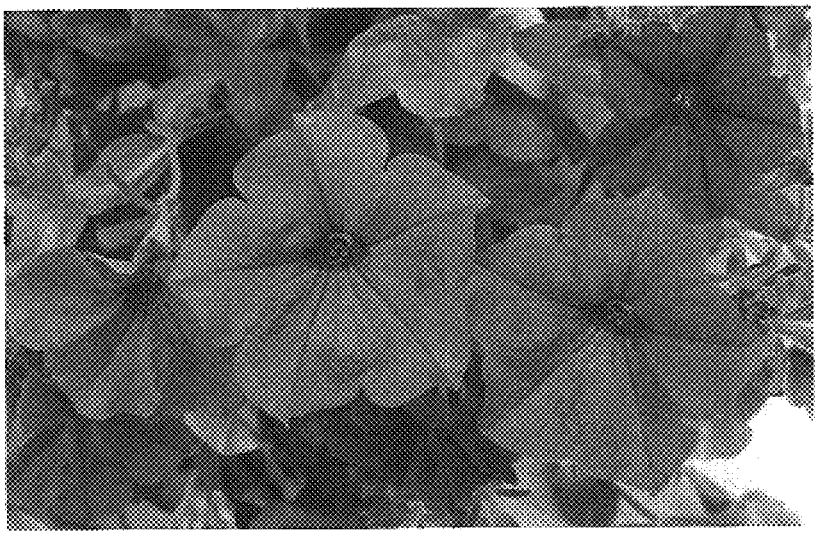

* * * * *